United States Patent
Justis et al.

(10) Patent No.: US 7,981,115 B2
(45) Date of Patent: Jul. 19, 2011

(54) INSTRUMENTS AND METHODS FOR SIZING A CONNECTING ELEMENT FOR POSITIONING ALONG A BONY SEGMENT

(75) Inventors: Jeff R. Justis, Collierville, TN (US); John D. Pond, Jr., Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 875 days.

(21) Appl. No.: 11/786,157

(22) Filed: Apr. 11, 2007

(65) Prior Publication Data

US 2008/0255575 A1 Oct. 16, 2008

(51) Int. Cl.
*A61B 17/58* (2006.01)
(52) U.S. Cl. ............... 606/102; 606/90; 606/105
(58) Field of Classification Search ........... 606/90, 606/102, 104
See application file for complete search history.

(56) References Cited

U.S. PATENT DOCUMENTS

| | | | |
|---|---|---|---|
| 4,271,836 A | 6/1981 | Bacal et al. | |
| 4,846,194 A | 7/1989 | Sabia | |
| 5,180,388 A | 1/1993 | DiCarlo | |
| 5,188,121 A | 2/1993 | Hanson | |
| 5,291,901 A | 3/1994 | Graf | |
| 5,309,648 A | 5/1994 | Allard et al. | |
| 5,376,093 A | 12/1994 | Newman | |
| 5,658,286 A | 8/1997 | Sava | |
| 5,704,937 A | 1/1998 | Martin | |
| 5,836,937 A | 11/1998 | Holmes | |
| RE36,221 E | 6/1999 | Breard et al. | |
| 6,427,351 B1 | 8/2002 | Matthews et al. | |
| 6,607,530 B1 | 8/2003 | Carl et al. | |
| 6,923,811 B1 | 8/2005 | Carl et al. | |
| 7,011,658 B2 * | 3/2006 | Young | 606/258 |
| 2004/0059333 A1 | 3/2004 | Carl et al. | |
| 2004/0138662 A1 | 7/2004 | Landry et al. | |
| 2004/0143265 A1 | 7/2004 | Landry et al. | |
| 2004/0172022 A1 | 9/2004 | Landry et al. | |
| 2004/0267279 A1 * | 12/2004 | Casutt et al. | 606/104 |
| 2005/0021040 A1 * | 1/2005 | Bertagnoli | 606/90 |
| 2005/0070917 A1 * | 3/2005 | Justis | 606/104 |
| 2005/0273167 A1 | 12/2005 | Triplett et al. | |
| 2006/0036244 A1 | 2/2006 | Spitler et al. | |
| 2006/0052795 A1 | 3/2006 | White | |
| 2006/0079894 A1 | 4/2006 | Colleran et al. | |
| 2006/0084993 A1 | 4/2006 | Landry et al. | |
| 2006/0106380 A1 | 5/2006 | Colleran et al. | |
| 2006/0106381 A1 | 5/2006 | Ferree | |
| 2006/0142761 A1 | 6/2006 | Landry et al. | |
| 2006/0173454 A1 | 8/2006 | Spitler et al. | |

* cited by examiner

*Primary Examiner* — Thomas C Barrett
*Assistant Examiner* — Michael T Schaper

(57) ABSTRACT

Instruments and methods for determining the spacing between locations in an animal subject are employed to size a connecting element to secure along a bony segment in the animal subject. The instruments and methods include a measuring instrument mountable to proximal ends of extensions extending from anchors engaged to the bony segment. The measuring instrument is configured to provide an indication of the spacing between the anchors even if the extensions are in non-parallel relation to one another.

17 Claims, 9 Drawing Sheets

INSTRUMENTS AND METHODS FOR SIZING A CONNECTING ELEMENT FOR POSITIONING ALONG A BONY SEGMENT

BACKGROUND

Various devices and methods for stabilizing bony segments have been used for many years. For example, the fracture of an elongated bone, such as a femur or humerus, can be stabilized by securing a plate to the fractured bone across the fracture. The plate extends across the fractured area and thus stabilizes the fractured components of the bones relative to one another in a desired position. When the fracture heals, the plate can be removed or left in place, depending on the type of plate that is used.

Another type of stabilization technique uses one or more elongated rods extending between components of a bony segment and secured to the bony segment to stabilize the components relative to one another. The components of the bony segment are exposed and one or more bone engaging fasteners are placed into each component. The elongated rod is then secured to the bone engaging fasteners in order to stabilize the components of the bony segment.

One problem associated with the above described stabilization structures is that the skin and tissue surrounding the surgical site must be cut, removed, and/or repositioned in order for the surgeon to access the location where the stabilization device is to be installed. This repositioning of tissue causes trauma, damage, and scarring to the tissue. There are also risks that the tissue will become infected and that a long recovery time will be required after surgery for the tissue to heal.

Minimally invasive surgical techniques are particularly desirable in, for example, spinal and neurosurgical applications because of the need for access to locations within the body and the potential trauma to vital intervening tissues. The development of percutaneous minimally invasive spinal procedures has yielded a major improvement in reducing trauma, recovery time and post-operative pain. The benefits of minimally invasive techniques have also found application in surgeries for other locations in the body where it is desirable to minimize tissue disruption.

One potential disadvantage associated with minimally invasive techniques is that the tissue can obstruct access and visualization of the implantation location for an implant in the body of the patient. Accordingly, the optimally sized implant for implantation between anchors or other structures in the patient may not be readily determinable. While minimally invasive techniques have yielded benefits, there remains a need for instruments and methods that facilitate application of minimally invasive procedures during surgery.

SUMMARY

The present invention relates to instruments and methods for determining the spacing between locations in an animal subject to size, for example, a connecting element to secure along a bony segment in the animal subject. The instruments and methods can be employed in minimally invasive surgical procedures.

According to one aspect, a system for measuring spacing between first and second locations in an animal subject includes a pair of anchor extensions and a measuring instrument mountable to proximal ends of the anchor extensions. The anchor extensions include distal ends engageable in the animal subject in association with a respective one of the locations. The measuring instrument includes first and second articulating mechanisms that are engageable to and movable relative to a respective one of the pair of anchor extensions. The measuring instrument further includes an indicator extending between and connecting the first and second articulating mechanisms to one another. The indicator includes means for measuring the spacing between the first and second articulating mechanisms to provide an indication of the spacing between the first and second locations.

According to another aspect, a system for measuring spacing between first and second locations in an animal subject comprises a pair of anchor extensions and a measuring instrument mounted to proximal ends of the anchor extensions. The anchor extensions include distal ends engageable in the animal subject in association with a respective one of the locations. The measuring instrument includes first and second articulating means engaging a respective one of the pair of anchor extensions. The first and second articulating means each further includes a corresponding alignment member with the first and second articulating means being operable to move the corresponding alignment member around the respective anchor extension and position the corresponding alignment member in alignment with a respective one of the locations. The measuring instrument further includes an indicator extending between and connecting the alignment members to measure a spacing between the alignment members to provide an indication of the spacing between the first and second locations in the animal subject.

According to another aspect, a method for determining the spacing between first and second locations in an animal subject comprises: engaging first and second anchors to a bony segment; engaging first and second anchor extensions to respective ones of the first and second anchors; mounting a measuring instrument to proximal ends of the first and second anchor extensions outside the animal subject; rotating the measuring instrument about each of the first and second anchor extensions to align first and second alignment members located outside the animal subject with the first and second locations in the animal subject; and measuring the spacing between the first and second alignment members to determine the spacing between the first and second locations.

Related features, aspects, embodiments, objects and advantages of the present invention will be apparent from the following description.

DESCRIPTION OF THE ILLUSTRATED EMBODIMENTS

Figure 1:
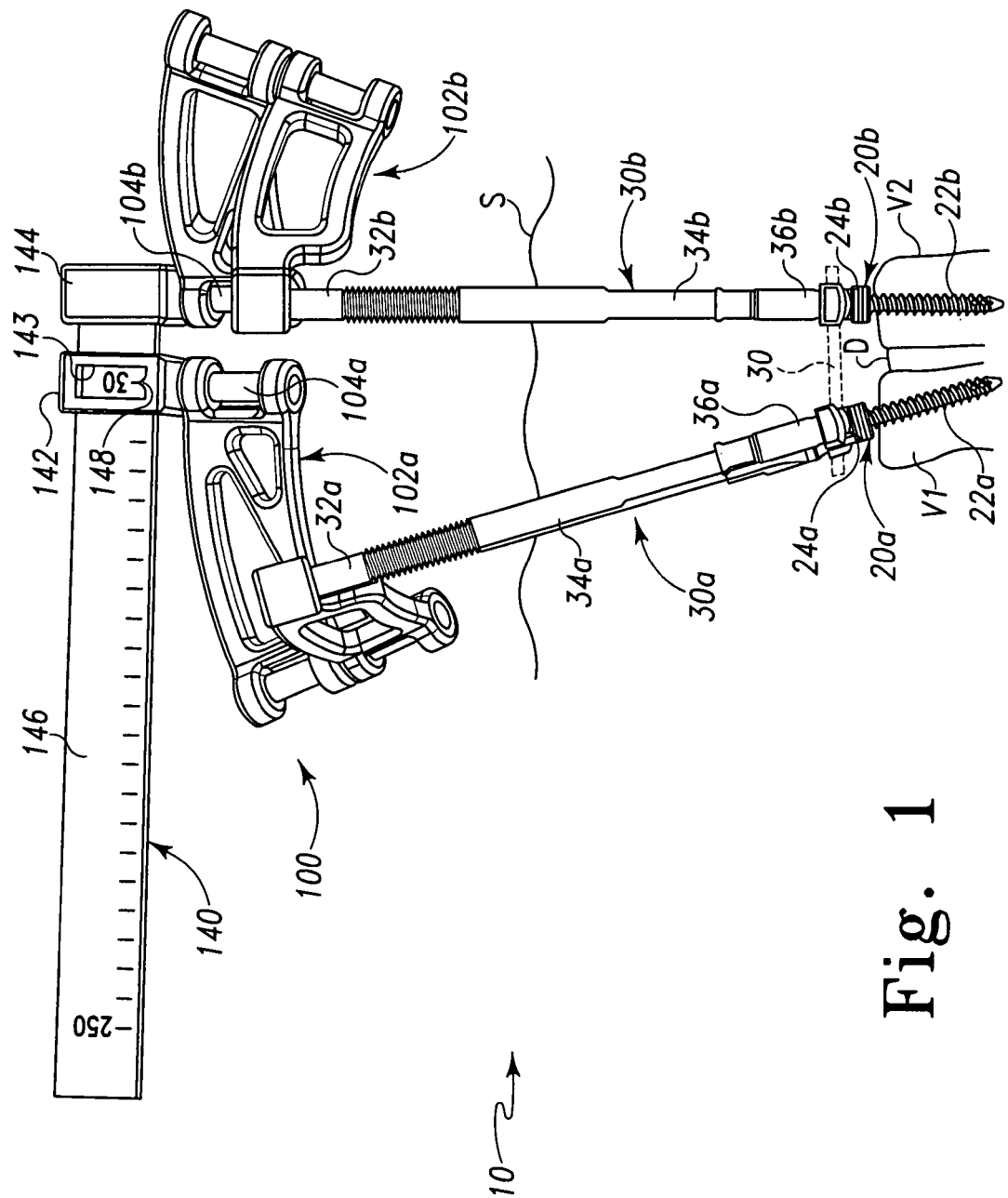
FIG. 1 is a perspective view looking toward the side of a spinal column segment with anchors engaged thereto, anchor extensions extending proximally from the anchors and a measuring instrument engaged to proximal ends of the anchor extensions and oriented to provide an indication of the spacing between the anchors.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Instruments and methods are provided for determining the length of a connecting element to implant along a bony segment in a patient are provided. The connecting element can be positioned between first and second anchors engaged to respective ones of first and second bony elements of the bony segment. First and second anchor extensions extend proximally from respective ones of the first and second anchors to proximal ends of the anchors extensions that are remote from the respective anchor. A measuring instrument is mounted to the proximal ends of the anchor extensions. The measuring instrument includes first and second articulating mechanisms each being movable relative to the respective anchor extension to align an alignment member of the articulating mechanism with a respective one of the first and second anchors. The measuring instrument also includes an indicator extending between the alignment members to provide an indication of the spacing between the alignment members. The measuring instrument provides an indication of the distance or spacing between the first and second anchors based on the relative position of the alignment members even if the anchor extensions extend in non-parallel relation to one another.

In one application, the measuring instrument is mounted between the proximal ends of first and second anchor extensions extending from first and second anchors. The anchor extensions are movable relative to the bony structure to which the respective anchor extension is mounted via the respective anchor, and the measuring instrument includes articulating mechanisms that position alignment members in a desired position relative to the anchors regardless of the orientation of the anchor extensions relative to one another. The spacing between the alignment members provides an indication of the spacing between the anchors, which can then be employed to select or modify a connecting element of appropriate length for connection between the anchors.

Referring to FIG. 1, one embodiment of a system 10 is shown with first and second anchors 20a, 20b having first and second anchors extensions 30a, 30b, respectively, engaged thereto. Anchors extensions 30a, 30b extend proximally from a respective one of the anchors 20a, 20b to a proximal end of the anchor extensions that is spaced from the anchors 20a, 20b. In one embodiment, the length of anchor extensions 30a, 30b locates the proximal end of the anchor extensions outside the body of the patient proximally of skin S while anchors 20a, 20b are engaged to first and second vertebrae V1, V2 of a bony segment.

Figure 2:
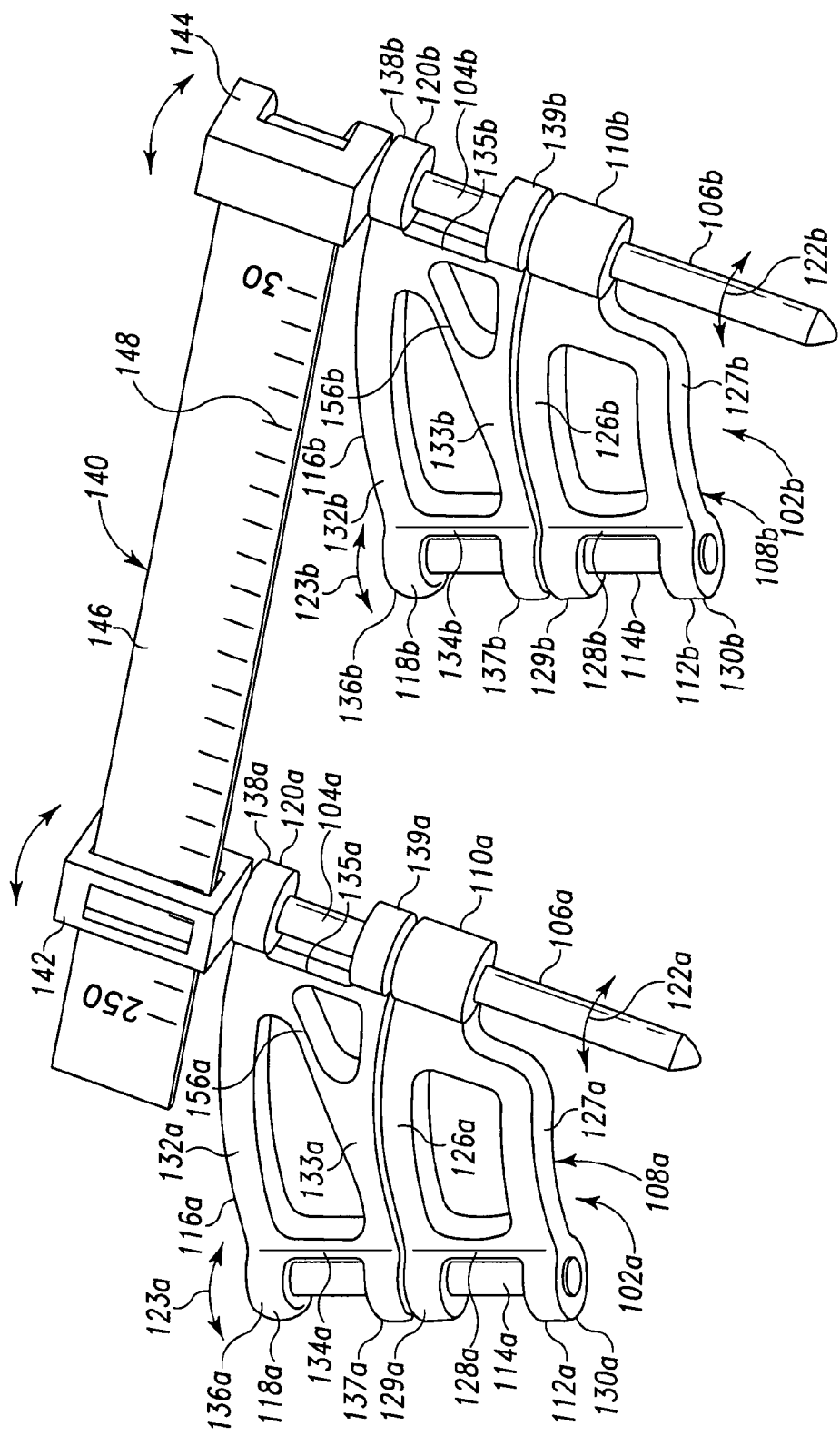
FIG. 2 is a perspective view of the measuring instrument of FIG. 1 in another orientation for measuring anchor extensions in parallel relation to one another.

Measuring instrument 100 includes first and second articulating mechanisms 102a, 102b mounted to respective ones of the anchor extensions 30a, 30b. As also shown in FIG. 2, indicator 140 extends between and is engaged to articulating mechanisms 102a, 102b. Articulating mechanisms 102a, 102b include alignment members 104a, 104b, respectively, that are positionable into alignment with the respective anchors 20a, 20b by manipulating articulating mechanisms 102a, 102b relative to the respective anchor extension 30a, 30b. When alignment members 104a, 104b are so aligned, indicator 140 provides an indication or measurement of the length or spacing between alignment members 104a, 104b, thus providing an indication of the spacing between anchors 20a, 20b so that the appropriately sized connecting element 18 can be selected or formed and positioned between and engaged to anchors 20a, 20b.

Measuring instrument 100 allows the surgeon to measure the appropriate or optimal length of connecting element 18 between anchors 20a, 20b even if anchors 20a, 20b are obscured by skin S and tissue between the skin and the target location for connecting element 18. In the illustrated embodiment of FIG. 1, anchors 20a, 20b are mounted to vertebrae V1, V2 of one or more spinal motion segments including disc space D between vertebrae V1, V2. Anchor extensions 30a, 30b extend from the respective anchor 20a, 20b through the tissue so that its associated proximal end 32a, 32b is located proximally of skin S for access by the surgeon. Anchors extensions 30a, 30b include an elongated body 34a, 34b extending from the proximal end 32a, 32b to an opposite distal end 36a, 36b. The distal ends 36a, 36b are removably coupled to the respective anchor 20a, 20b. Anchors extensions 30a, 30b also include an internal passage that provides access to the respective anchor 20a, 20b. Engaging members such as set screws, caps, or other devices and/or driving instruments can be moved through the internal passage to secure the engaging member to the respective anchor 20a, 20b to couple connecting element 18 thereto. The passages of anchor extensions 30a, 30b also open at proximal ends 32a, 32b to facilitate mounting of measuring instrument 100 to anchor extensions 30a, 30b.

Figure 3:
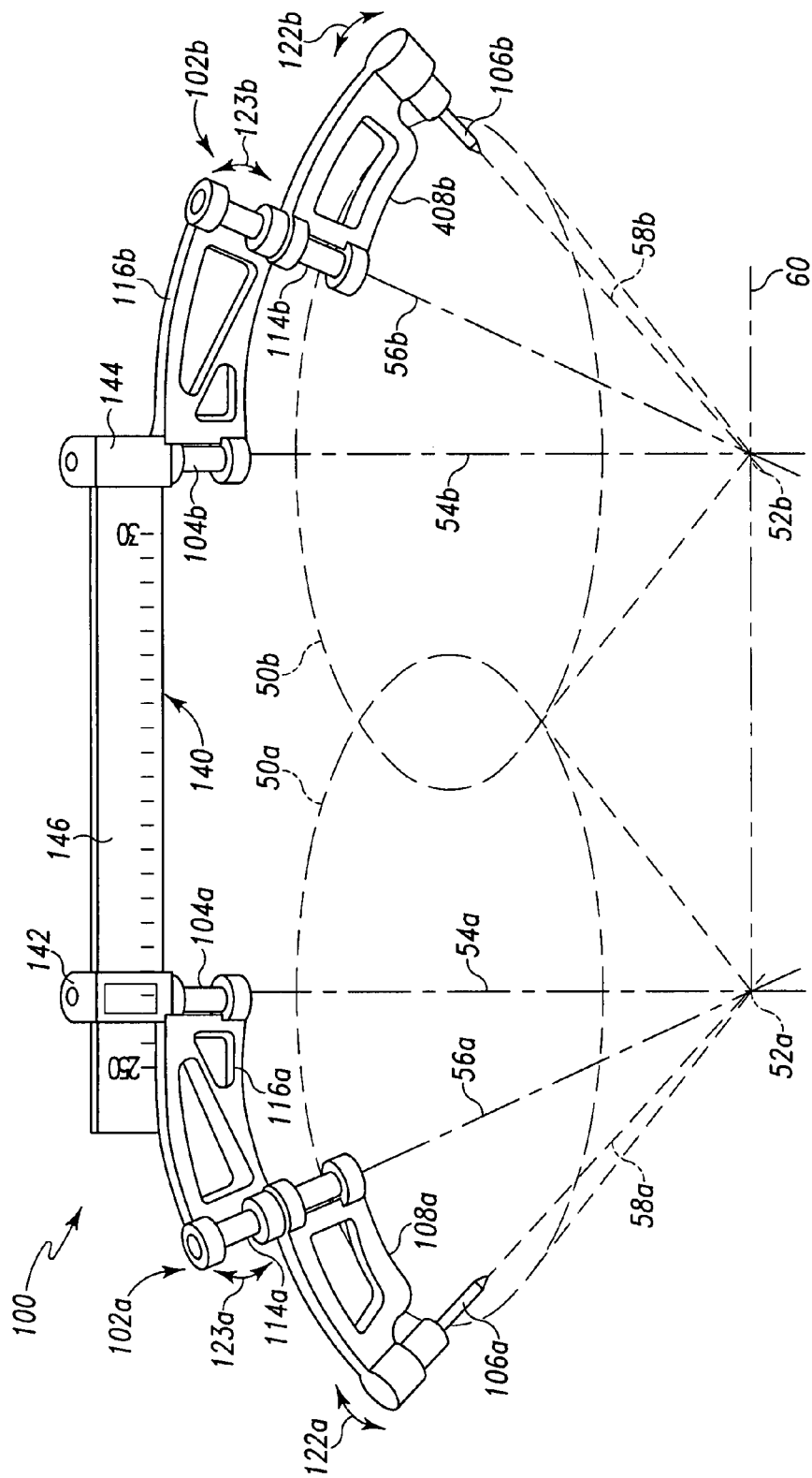
FIG. 3 is another perspective view showing another orientation of the measuring instrument and a diagram of the range of motion of the anchor extensions relative to the anchors and various potential orientations of the measuring instrument relative to the anchor extensions.
Figure 4:
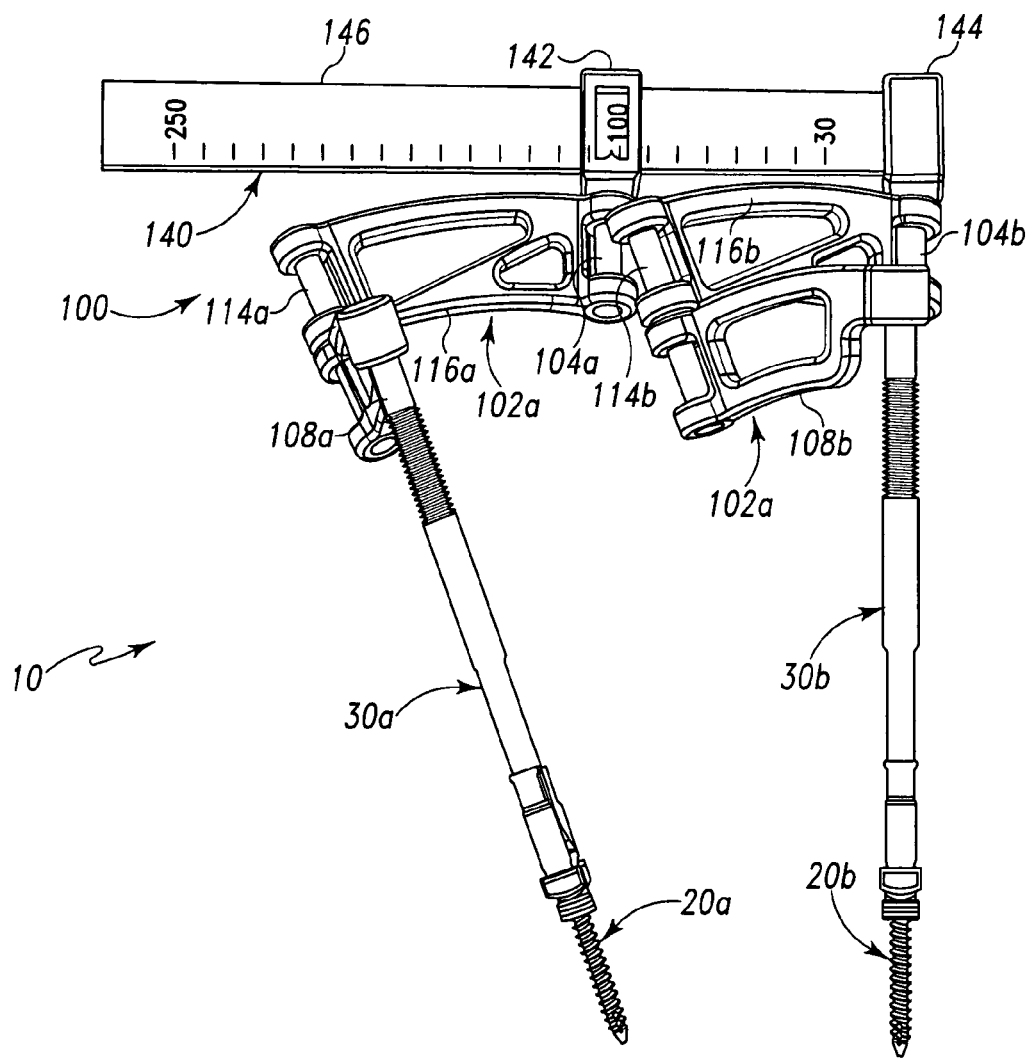
FIG. 4 is another perspective view of an arrangement engageable to a spinal column segment that includes anchors engageable to bony elements, anchor extensions extending proximally from the anchors in non-parallel relation, and the measuring instrument engaged to the proximal ends of the anchor extensions and positioned to provide an indication of the spacing between the anchors.
Figure 5:
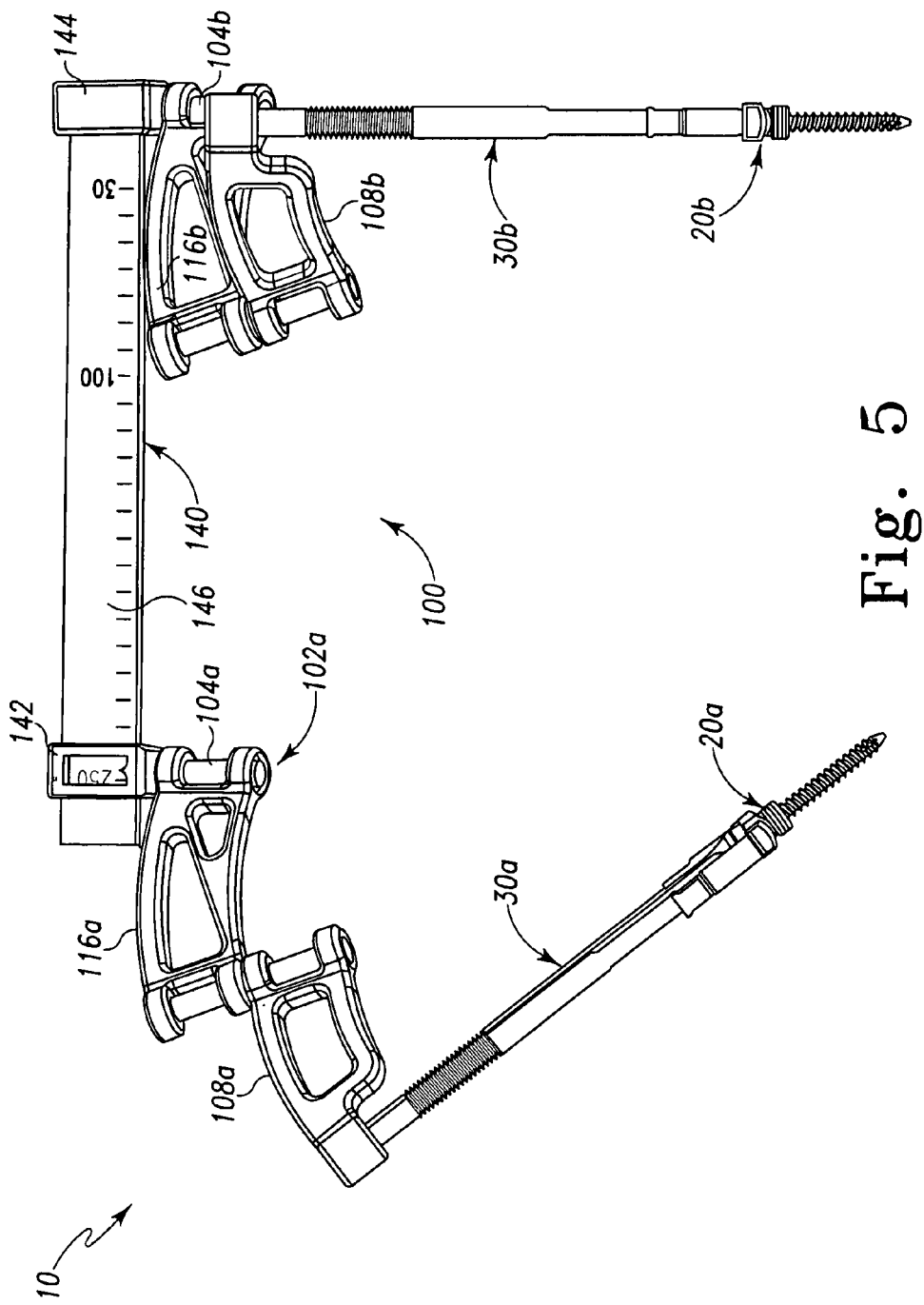
FIG. 5 is a perspective view looking toward the side of a pair of anchor extensions engaged to anchors and positioned in non-parallel relation to one another and the measuring instrument extending between the proximal ends of the anchor extensions in an orientation to provide an indication of the spacing between the anchors engaged to the anchor extensions.

Anchor extensions 30a, 30b are each positionable into the patient in an orientations relative to the bony segment to which it is attached at any location about or within the respective cone 50a, 50b shown diagrammatically in FIG. 3. The point of each cone 50a, 50b represents the locations 52a, 52b about which anchors extensions 30a, 30b pivot when mounted to anchors 20a, 20b and the location of receiver portions 24a, 24b in the patient to which the connecting element 18 is engaged. In one embodiment, anchors 20a, 20b include a distal bone engaging portion 22a, 22b and a proximal receiver portion 24a, 24b (FIG. 1). Bone engaging portion 22a, 22b is configured to engage bony material, and can be in the form of a bone screw, hook, staple, anchor, interbody device, intrabody device, or any other suitable bone anchor structure. Receiver portions 24a, 24b extend proximally from the respective bone engaging portion 22a, 22b and are located to receive or engage the connecting element 18 along the bony segment to which the bone engaging portions are attached. In one embodiment, receiver portions 24a, 24b are U-shaped saddles that are pivotally mounted to the respective bone engaging portion 22a, 22b. In another embodiment, receiver portions 24a, 24b are fixed relative to the respective bone engaging portion 22a, 22b.

Distal ends 36a, 36b of anchor extensions 30a, 30b are mounted to the respective receiver portion 24a, 24b and the anchor extensions 30a, 30b are pivotal by pivoting the receiver portion 24a, 24b relative to the respective bone engaging portion 22a, 22b. The receiver portions 24a, 24b can include internal and/or external threads or other structure to engage an engaging member such as a set screw, nut, cap or other device to secure connecting element 18 in or on the respective receiver portion 24a, 24b. The receiver portions can be open so that connecting element 18 can be side-loaded or end-loaded therein from a proximal, medial or lateral side of receiver portion. In another embodiment, the receptacle of the receiver portion is enclosed by the receiver portion and the receiver portion includes bores extending into the receptacle for insertion of the connecting element therethrough in an endwise manner. The receiver portion can be fixed to the bone engaging portion of the anchor, or movable relative to the bone engaging portion to provide multiple angular or translational arrangements between the receiver portion and the bone engaging portion.

In one embodiment, anchor extensions 30a, 30b include an internal sleeve having a pair of arms at distal end 36a, 36b that are movable toward and away from one another to clampingly engage the respective receiver portion 24a, 24b therebetween. The anchor extensions 30a, 30b further include an external sleeve arranged about and movable relative to the inner sleeve to secure and release the distal arms to the respective receiver portions 24a, 24b. Other embodiments contemplate any suitable coupling arrangement for securing the anchor extensions 30a, 30b to the anchors 20a, 20b. Further examples of suitable anchor extensions, engagement relationships between anchor extensions and anchors, and techniques for positioning the connecting element in position relative to the anchors are discussed in U.S. Patent Application Publication No. 2002/0161368 published on Oct. 31, 2002; U.S. patent application Ser. No. 11/213,473 filed on Aug. 26, 2005; and U.S. patent application Ser. No. 11/348,999 filed on Feb. 7, 2006; each of which is incorporated herein by reference in its entirety.

Referring now to FIG. 2, measuring instrument 100 will be further discussed. Measuring instrument 100 includes first and second mounting members 106a, 106b that mount the respective articulating mechanism 102a, 102b to the corresponding anchor extensions 30a, 30b. Articulating mechanisms 102a, 102b include first and second arms 108a, 108b extending from respective ones of the mounting members 106a, 106b. First and second arms 108a, 108b each have a first end 110a, 110b from which the respective mounting member 106a, 106b extends in a distal direction. First and second arms 108a, 108b extend from first ends 110a, 110b thereof to an opposite second end 112a, 112b. The second ends 112a, 112b each include a linking member 114a, 114b mounted thereto and extending therefrom in a proximal direction to a second arm 116a, 116b. Second arms 116a, 116b include a first end 118a, 118b mounted to and rotatable about a respective one of the linking members 114a, 114b. Second arms 116a, 116b extend from first end 118a, 118b thereof to an opposite second end 120a, 120b. Alignment members 104a, 104b extend along the respective second end 120a, 120b and are movable with the articulating mechanisms 102a, 102b from a position in alignment with the respective mounting member 106a, 106b as shown in FIG. 2 in any direction 360 degrees about linking members 114a, 114b as indicated by arrows 123a, 123b.

Mounting members 106a, 106b are positionable into the proximal opening of the passage of the respective anchor extensions 30a, 30b to mount measuring instrument 100 to anchor extensions 30a, 30b. In the illustrated embodiment, mounting members 106a, 106b are elongated pins with distal tapered tips to facilitate insertion into the anchor extensions 30a, 30b. Once positioned in the respective anchor extension 30a, 30b, the associated first arm 108a or second arm 108b can be rotated relative to the respective anchor extensions 30a, 30b by rotating the respective mounting members 106a, 106b in the passage of the anchor extensions 30a, 30b, as indicated by arrows 122a, 122b. Other embodiments contemplate other means for mounting measuring instrument 100 to anchor extensions 30a, 30b, including collars, clamps, bushings, sleeves, and other devices, for example.

First arm 108a of articulating mechanism 102a includes an elongate body that has first and second support members 126a, 127a and first arm 108b of articulating mechanism 102b includes an elongate body that has first and second support members 126b, 127b. The first and second support members separate from one another at the respective first end 110a, 110b and extend to the corresponding second end 112a, 112b. A strut 128a, 128b links the first and second support members together adjacent the respective second end 112a, 112b. Ears 129a, 130a extend outwardly from strut 128a to receive the linking member 114a, and ears 129b, 130b extend outwardly from the strut 128b to receive the linking member 114b. The spaced support members provide a rigid support that minimizes or prevents deflection of the articulating mechanisms 102a, 102b during use. Other embodiments contemplate a single support member along first arms 108a, 108b, or first arms 108a, 108b that include more than two support members and/or more than one strut.

Second arm 116a of articulating mechanism 102a includes an elongate body that has third and fourth support members 132a, 133a and second arm 108b of articulating mechanism 102b includes an elongate body that has third and fourth support members 132b, 133b. The third and fourth support members extend generally parallel to one another between opposite end members 134a, 135a of second arm 116a and opposite end members 134b, 135b of second arm 116b. End members 134a, 134b include ears 136a, 137a and ears 136b 137b, respectively, extending therefrom to which respective ones of the linking members 114a, 114b are rotatably mounted. End members 135a, 135b include ears 138a, 139a and ears 138b 139b, respectively, extending therefrom to which respective ones of the alignment members 104a, 104b are mounted. A diagonal strut 156a, 156b extends from the respective support member 133a, 133b to the junction of the associated support member 132a, 132b and strut 135a, 135b of each of the second arms 116a, 116b.

Figure 6:
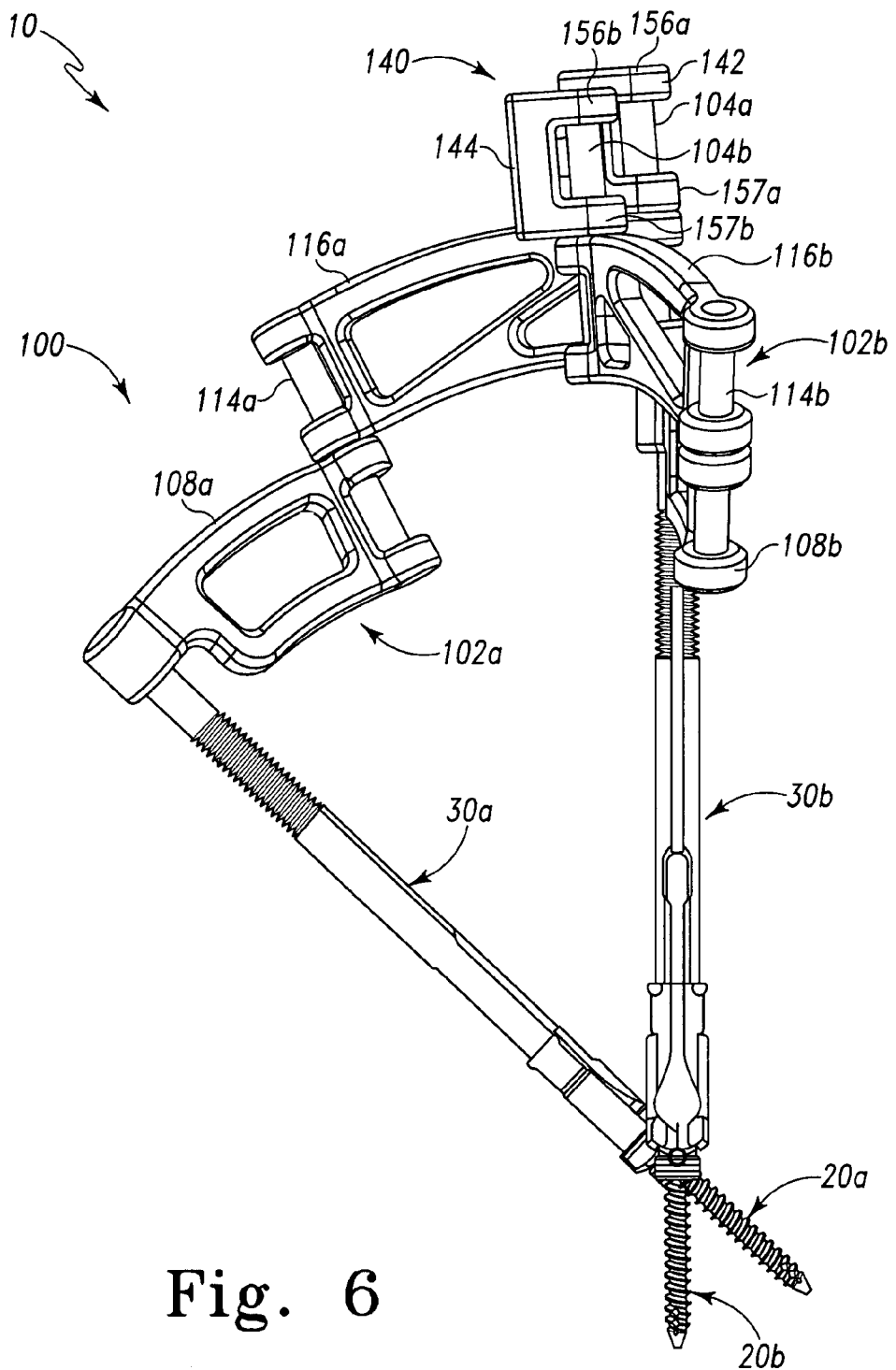
FIG. 6 is another perspective view of the arrangement of FIG. 5 looking thereon from the right hand side.

Alignment members 104a, 104b extend proximally from respective ears 138a, 138b to receive a respective one of the coupling members 142, 144 of indicator 140 thereon. Coupling member 144 is rotatably mounted about alignment member 104b and includes indicator arm 146 extending therefrom. Indicator arm 146 is fixed relative to coupling member 144, and extends through coupling member 142. Coupling member 142 is rotatably mounted about alignment member 104a. As shown in FIG. 6, coupling members 142, 144 include ear portions 156a, 157a and ear portions 156b, 157b, respectively, rotatably mounted about the respective proximal portion of corresponding alignment member 104a, 104b. Coupling member 142 is movable along indicator arm 146 so its location along the scale 148 of indicator arm 146 provides an indication of the separation distance between the alignment members 104a, 104b, and thus an indication of the spacing of locations 52a, 52b defined by the receiver portions 24a, 24b of anchors 20a, 20b when measuring instrument 100 is mounted to the proximal ends of anchor extensions 30a, 30b. In the illustrated embodiment, coupling member 142 includes a window 143 and a pointer 145 in window 143 and in alignment with alignment member 104a. Scale 148 is observable through window 143 along with the location of pointer 145 along scale 148, such as shown in FIG. 1.

In the illustrated embodiment, first arms 108a, 108b and second arms 116a, 116b are curved between their respective first and second ends and in a manner such that the concave side of the curvature is oriented distally toward the anchor extensions 30a, 30b when mounted thereto. Linking members 114a, 114b and alignment members 104a, 104b extend transversely to the respective first arms 108a, 108b and second arms 116a, 116b to, as shown in FIG. 3, lie along axes that intersect the locations 52a, 52b adjacent to distal ends 36a, 36b of anchor extensions 30a, 30b. In FIG. 3, alignment member 104a extends along alignment axis 54a, and alignment member 104b extends along alignment axis 54b. Similarly, linking member 114a extends along linking axis 56a, and linking member 114b extends along linking axis 56b. Alignment axis 54a and linking axis 56a intersect at location 52a, and alignment axis 54b and linking axis 56b intersect at location 52b. The intersection between these axes and locations 52a, 52b is maintained regardless of the relative positioning of first arms 108a, 108b and second arms 116a, 116b when measuring instrument 100 is mounted to anchor extensions 30a, 30b with mounting members 106a, 106b.

Mounting members 106a, 106b, when mounted to the respective anchor extension 30a, 30b, extend along a mounting axis 58a, 58b that coincides with the central axis of the respective anchor extension 30a, 30b and intersects the respective location 52a, 52b. As indicated by arrows 122a, 122b, mounting members 106a, 106b are rotatable 360 degrees in the proximal end of the respective anchor extension regardless of the location of the proximal end of the respective anchor extensions within the base of the associated cone 50a, 50b so long as clearance is maintained with skin S and first arms 108a, 108b. Linking axes 56a, 56b are thus positionable relative to the associated anchor extension 30a, 30b and mounting axis 58a, 58b at any position about the perimeter of a cone having a base with a radius defined by the length of the respective first arm 108a, 108b between its mounting member 106a, 106b and the respective linking member 114a, 114b. Similarly, alignment axes 54a, 54b are rotatable 360 degrees about the associated linking member 114a, 114b as indicated by arrows 123a, 123b. Alignment axes 54a, 54b are positionable at any position about the perimeter of a cone having a base with a radius defined by the length of the second arms 116a, 116b between linking members 114a, 114b and the respective alignment member 104a, 104b.

Figure 7:
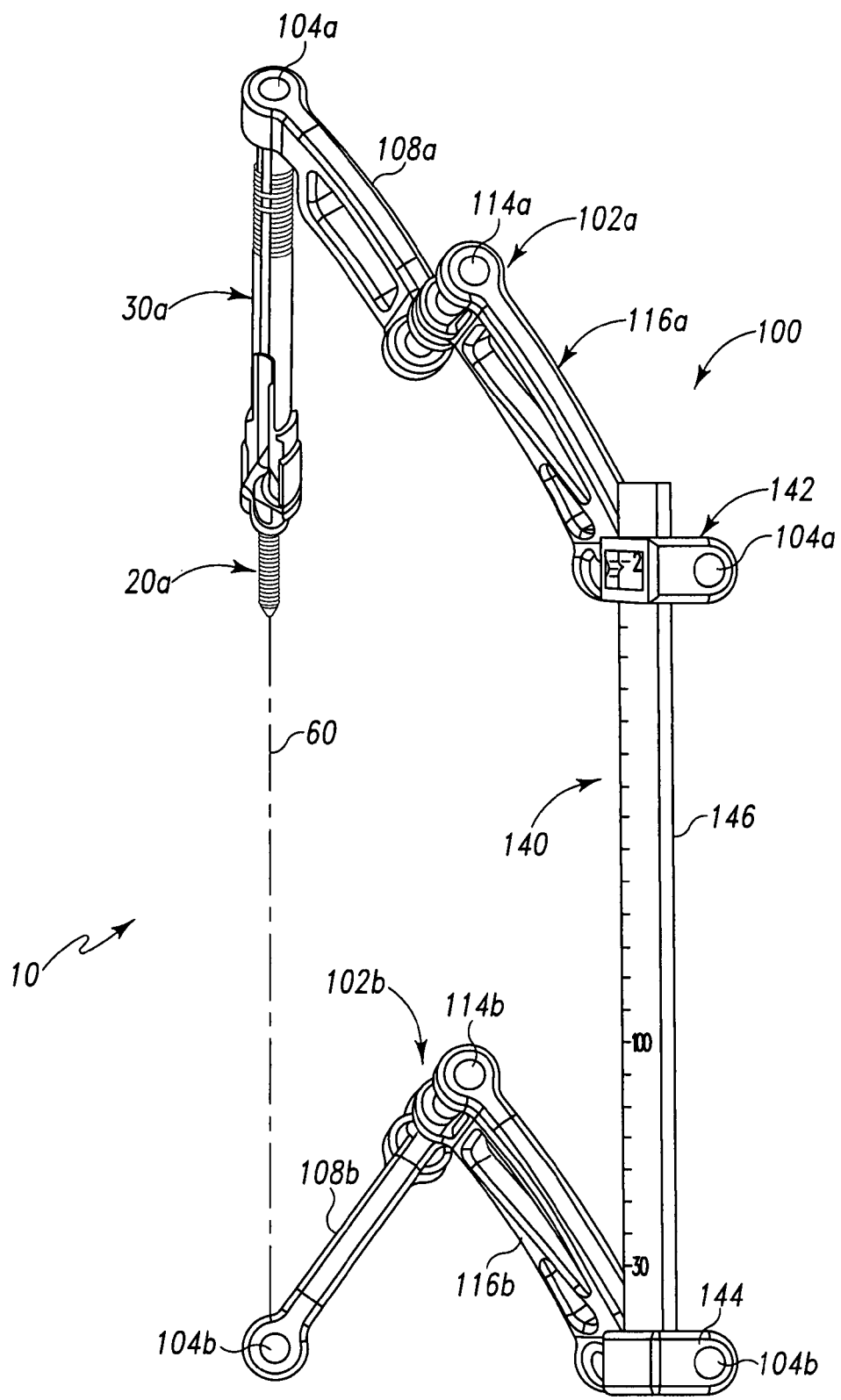
FIG. 7 is another perspective view of the arrangement of FIG. 5 looking downwardly thereon in the distal direction.

Along with FIG. 1, FIGS. 4-7 show various non-parallel orientations between anchor extensions 30a, 30b engaged to anchors 20a, 20b and measuring instrument 100 extending between the anchor extensions 30a, 30b. In use, anchors 20a, 20b are engaged to bony elements such as vertebrae of the spinal column. Anchor extensions 30a, 30b are attached to the respective anchor 20a, 20b either prior to engagement of the anchor with the bony element or after it is engaged to the bony element. Anchor extensions 30a, 30b can extend through skin and/or tissue of the patient so that the distal end 36a, 36b and the anchor 20a, 20b engaged thereto are not readily viewable by the surgeon or accessible to determine the optimal or desired length for connecting element 18 between anchors 20a, 20b. Measuring instrument 100 is mounted to the proximal ends of the anchor extensions 30a, 30b with the mounting members 106a, 106b positioned into the anchor extensions. Articulating mechanisms 102a, 102b are manipulated relative to the anchor extensions 30a, 30b to orient and position indicator arm 146 of indicator 140 in parallel arrangement with the path 60 extending between locations 52a, 52b defined by receiver portions 24a, 24b of anchors 20a, 20b, such as shown in FIG. 7. Furthermore, articulating mechanisms 102a, 102b are manipulated so that alignment members 104a, 104b are located in alignment with the positioning of locations 52a, 52b in the cephalad-caudal direction along the spinal column and in the direction along path 60. The measurement of the spacing between the alignment members 104a, 104b provided on the scale of indicator arm 46 provides an indication of the spacing between locations 52a, 52b in the patient. The measurement is then employed to select a connecting element 18 of the desired length, or used to modify the length of an existing connecting element 18, to fit the space between locations 52a, 52b.

Figure 8:
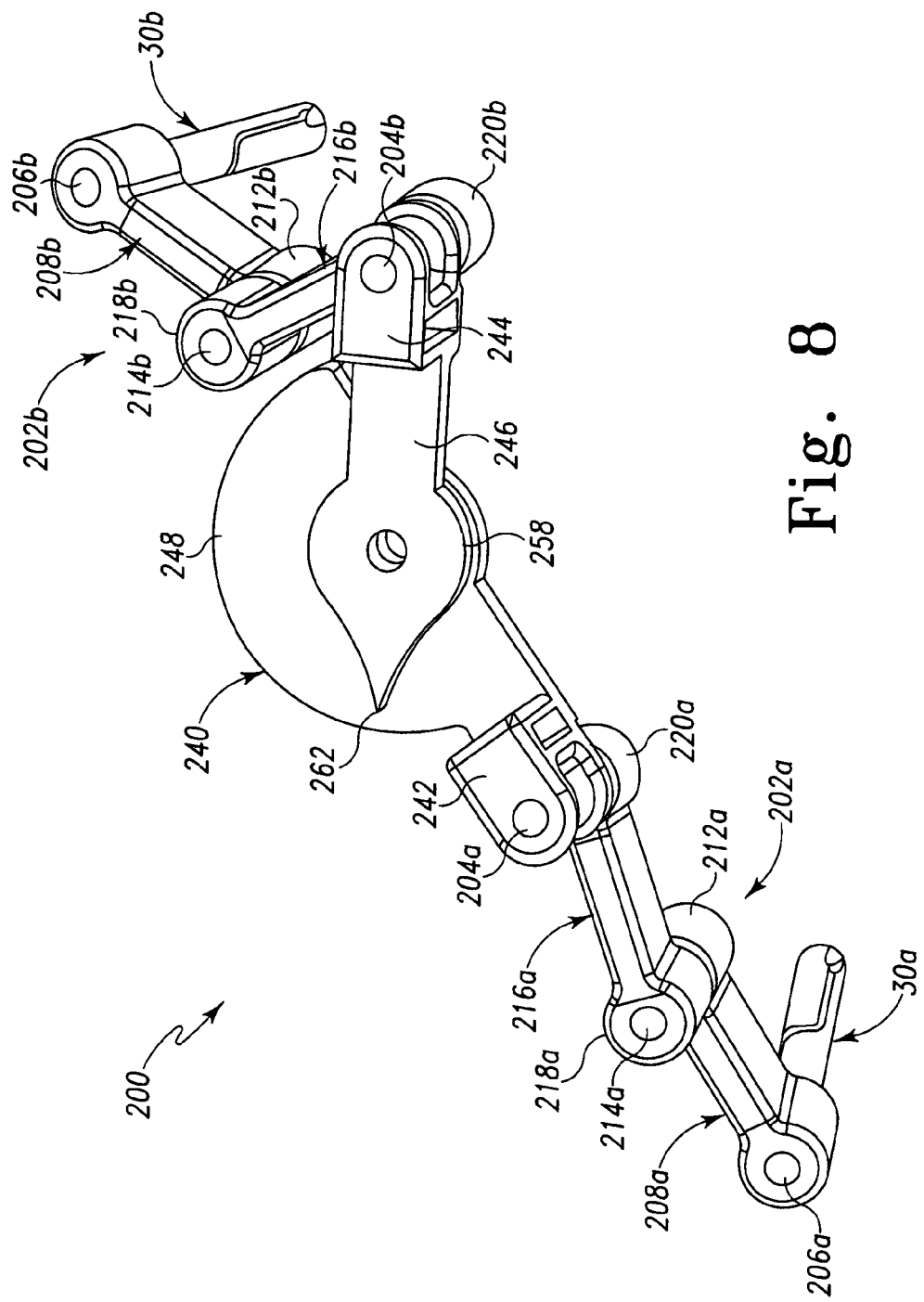
FIG. 8 is a perspective view of another embodiment measuring instrument mounted to a pair of anchor extensions.
Figure 9:
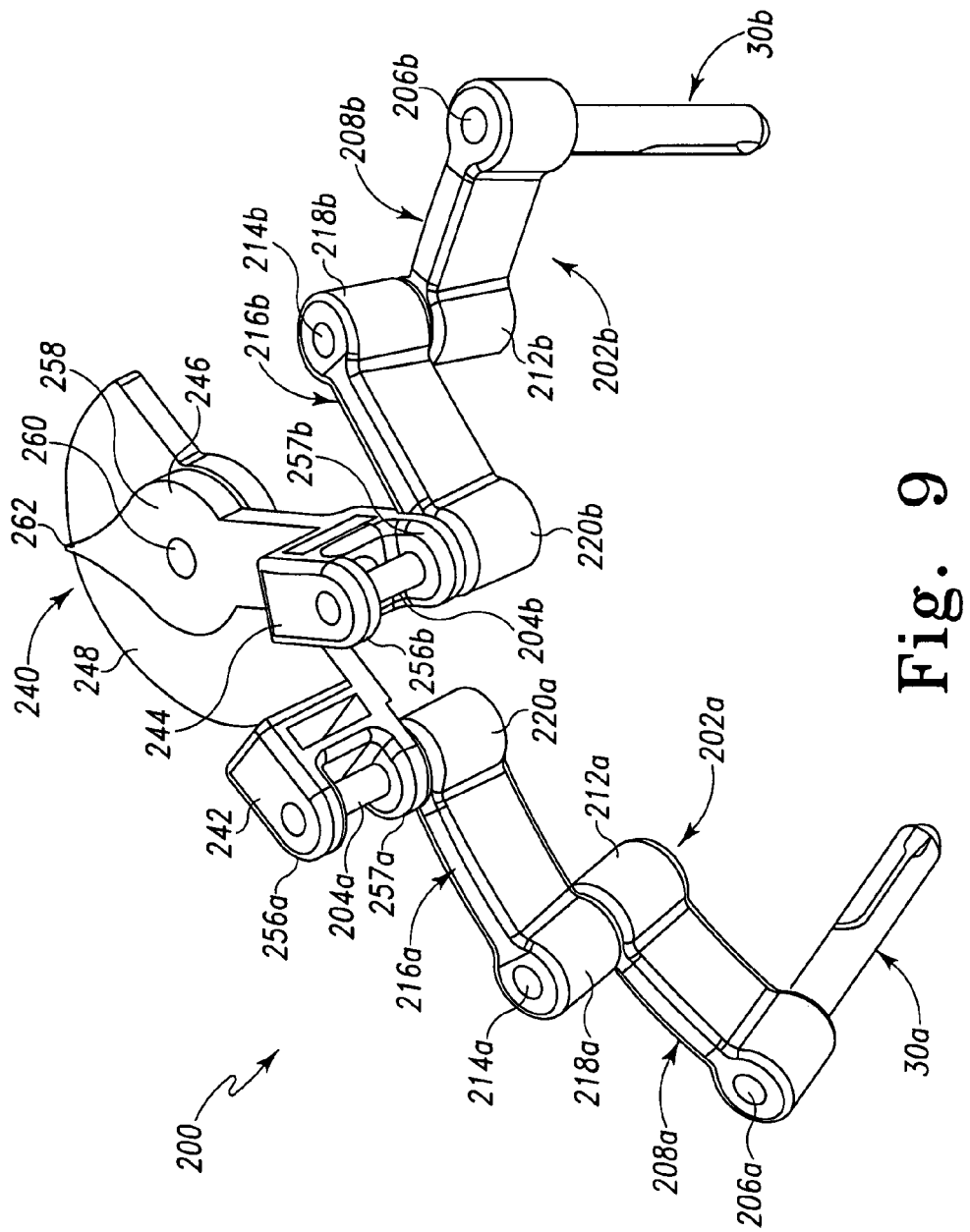
FIG. 9 is another perspective view of the measuring instrument of FIG. 8 with the anchor extensions and measuring instrument in another orientation.

Referring now to FIGS. 8-9, another embodiment measuring instrument 200 will be further discussed. Measuring instrument 200 is similar to measuring instrument 100 discussed above, and is mounted to anchor extensions 30a, 30b with mounting members 206a, 206b like mounting members 106a, 106b discussed above. Measuring instrument 200 includes articulating mechanisms 202a, 202b mounted to the corresponding anchor extension 30a, 30b. Articulating mechanisms 202a, 202b include first arms 208a, 208b extending from and transversely to respective ones of the mounting members 206a, 206b. First arms 208a, 208b extend from the respective anchor extensions 30a, 30b to an opposite second end 212a, 212b. The second ends 212a, 212b each include a linking member 214a, 214b mounted thereto and extending therefrom in a proximal direction to a respective one of the second arms 216a, 216b. Second arms 216a, 216b include a first end 218a, 218b mounted to and rotatable about a respective one of the linking members 214a, 214b. Second arms 216a, 216b extend from first end 218a, 218b thereof to an opposite second end 220a, 220b. Alignment members 204a, 204b extend along the respective second end 220a, 220b and are movable with the articulating mechanisms 202a, 202b from a position in alignment with the respective mounting member 206a, 206b in any direction 360 degrees about linking members 214a, 214b in the manner discussed above with respect to articulating mechanisms 102a, 102b of measuring instrument 100.

First arms 208a, 208b and second arms 216a, 216b of articulating mechanisms 202a, 202b each include an elongate body having a rod or shaft like form between its respective opposite ends. The ends of arms 208a, 208b, 216a, 216b each define a receptacle that receives the respective mounting member, linking member or alignment member therein. Mounting members 206a, 206b are configured to rotate in the respective anchor extension 30a, 30b. Alternatively, first arms 208a, 208b are rotatable about the respective mounting member 206a, 206b. Linking members 214a, 214b are secured in the receptacle at ends 212a, 212b of first arms 208a, 208b. Second arms 216a, 216b extend generally parallel with the respective first arms 208a, 208b and include receptacles at ends 218a, 218b that receive the respective linking member 214a, 214b so that second arms 216a, 216b are rotatable about the respective linking member 214a, 214b and relative to first arms 208a, 208b.

Alignment members 204a, 204b extend proximally from ends 220a, 220b and transversely to second arms 216a, 216b to rotatably receive a respective one of the coupling members 242, 244 of indicator 240 thereon. Coupling member 242 includes a scale member 248 extending therefrom that is fixed thereto. Coupling member 242 and scale member 248 are rotatable about alignment member 204a. Coupling member 244 is rotatably mounted about alignment member 204b and includes indicator arm 246 extending therefrom. Indicator arm 246 is fixed relative to coupling member 244. Coupling member 244 and indicator arm 246 are rotatable about alignment member 204b. Indicator arm 246 includes a central portion 258 rotatably mounted to scale member 248 with connection device 260. The outer end of indicator arm 246 includes a pointer 262 that moved along a scale formed along the outer perimeter of scale member 248 as pointer 262 is rotated relative to scale member 248 about pin 260. In one embodiment, connection device 260 is a pin or other suitable connector. In another embodiment, connection device is a removable pin, magnetic coupling, or other suitable device that permits attachment and detachment of indicator arm 246 to scale member 248. This allows the articulating mechanisms 202a, 202b to be separately mounted to the respective extensions 30a, 30b and then joined to one another by pivotally securing indicator arm 246 to scale member 248.

As shown in FIG. 9, coupling members 242, 244 include ear portions 256a, 257a and ear portions 256b, 257b, respectively, rotatably mounted about the respective proximal portion of corresponding alignment member 204a, 204b. Coupling member 244 is movable to pivot indicator arm 246 about pin 260 so that the location of pointer 262 along scale member 248 provides an indication of the separation distance between the alignment members 204a, 204b, and thus an indication of the spacing of locations 52a, 52b defined by the receiver portions 24a, 24b of anchors 20a, 20b when measuring instrument 200 is mounted to the proximal ends of anchor extensions 30a, 30b.

In the illustrated embodiment, first arms 208a, 208b and second arms 216a, 216b are curved between their respective first and second ends and in a manner such that the concave side of the curvature is oriented distally toward the anchor extensions 30a, 30b when mounted thereto. Non-curved arrangements are also contemplated. Linking members 214a, 214b and alignment members 204a, 204b extend transversely to the respective first arms 208a, 208b and second arms 216a, 216b and lie along axes that intersect the locations 52a, 52b adjacent to distal ends 36a, 36b of anchor extensions 30a, 30b in the manner discussed above with respect to measuring instrument 100 and as shown in FIG. 3. The intersection between these axes and locations 52a, 52b is maintained regardless of the relative positioning of first arms 208a, 208b and second arms 216a, 216b when measuring instrument 200 is mounted to anchor extensions 30a, 30b with mounting members 206a, 206b.

FIGS. 8-9 show various non-parallel orientations between anchor extensions 30a, 30b and measuring instrument 200 extending between the anchor extensions 30a, 30b. In use, anchors such as anchors 20a, 20b discussed above are engaged to bony elements such as vertebrae of the spinal column. Anchor extensions 30a, 30b are attached to the respective anchor either prior to engagement of the anchor with the bony element or after it is engaged to the bony element. Anchor extensions 30a, 30b can extend through skin and/or tissue of the patient so that their distal ends and the anchors engaged thereto are not readily viewable by the surgeon or accessible to determine the optimal or desired length for connecting element 18 between the anchors. Measuring instrument 200 is mounted to the proximal ends of the anchor extensions 30a, 30b with the mounting members 206a, 206b positioned into the anchor extensions. In one embodiment, articulating mechanisms 202a, 2002b are coupled to one another and mounted together to the anchor extensions 30a, 30b. In another embodiment, articulating mechanisms 202a, 202b are separate from one another and separately mounted to the respective extensions 30a, 30b, and then joined together at connection 260 between indicator arm 246 and scale member 248.

Articulating mechanisms 202a, 202b are manipulated relative to the anchor extensions 30a, 30b to orient and position alignment members 204a, 204b in alignment with the positioning of locations 52a, 52b in the cephalad-caudal direction along the spinal column and in the direction defined by path 60. The measurement of the spacing between the alignment members 204a, 204b provided on the scale of scale member 248 by indicator arm 246 provides an indication of the spacing between locations 52a, 52b in the patient. The measurement is then employed to select a connecting element 18 of the desired length, or used to modify the length of an existing connecting element 18, to fit the space between locations 52a, 52b and this between the anchors 20a, 20b.

In spinal surgical procedures, the selected connecting element 18 can be delivered to one or more vertebrae in an anterior approach, a posterior approach, a lateral approach, postero-lateral approach, a transforaminal approach, or an anterior-oblique approach, for example. Vertebrae V1, V2 can comprise all or a portion of the cervical, thoracic, lumbar and sacral vertebrae of the spinal column. In addition to stabilization of one or more spinal motion segments with connecting element 18, other spinal repair procedures can be performed as an additional procedure, including procedures to fuse vertebrae with one or more implants or bone graft, to replace one or more vertebral bodies, to repair annulus tissue, or to insert artificial disc components, for example. Applications in non-spinal procedures are also contemplated.

Connecting element 18 is rigid in one embodiment to prevent motion between the bony segments to which it is attached via the anchors 20a, 20b. In another embodiment connecting element 18 is fabricated from one or more components that are flexible or exhibit at least some flexibility or non-rigidity to permit motion of the stabilized vertebral level or levels. Some examples include extruded components, machined components, molded components, formed components, and milled components. Connecting element 18 can include any one or more of sheets, tethers, cords, planar members, bands, wires, cables, rods, bars, woven structures, or any other component capable of forming or being formed into the implant body. In a further form, connecting element 18 is resilient and/or elastic in whole or in part so it can assume various shapes during and after insertion and attachment while exhibiting a tendency to return to its natural form. In yet another form, connecting element 18 is substantially inelastic so that the shape achieved upon insertion or deformation is maintained.

Connecting element 18 can be made from any biocompatible material, material of synthetic or natural origin, and material of a resorbable or non-resorbable nature. Suitable examples of implant material include autograft, allograft or xenograft; tissue materials including soft tissues, connective tissues, demineralized bone matrix and combinations thereof; resorbable materials including polylactide, polyglycolide, tyrosinederived polycarbonate, polyanhydride, polyorthoester, polyphosphazene, calcium phosphate, hydroxyapatite, bioactive glass, collagen, albumin, fibrinogen and combinations thereof; and non-resorbable materials including polyethylene, polyester, polyvinyl alcohol, polyacrylonitrile, polyamide, polytetrafluorethylene, polyparaphenylene terephthalamide, cellulose, carbon-reinforced polymer composites, PEEK, shape memory alloys, titanium, titanium alloys, cobalt chrome alloys, stainless steel, and combinations thereof.

One specific example of a suitable anchor 20a, 20b is a multi-axial screw such as described in U.S. Pat. Nos. 5,797,911 and 5,879,350, each of which is incorporated herein by reference. Other examples for anchors 10 include uni-axial screws, bolts, clamps, hooks, and pins, for example. It is further contemplated that one or more of the anchors can include a multi-axial head and one or more of the other anchors include an uni-axial head. The anchors can be cannulated to facilitate placement over a guidewire and into the vertebra in minimally invasive procedures, or can be non-cannulated. Cannulated anchors can further include one or more fenestrations or openings for placement of bone cement or other material therethrough.

Pre-operative planning and image guided navigation of anchor placement and installation of connecting element 18 are also contemplated. The surgical techniques can employ any type of known imaging system to determine and locate optimum placement and orientation of the anchors in the bony structure and, if necessary, to locate skin locations for percutaneous puncture entry of the anchors and connecting element.

Anchor insertion can be monitored using any known viewing instrument or apparatus, and performed under any known surgical technique. For example, anchors 20a, 20b can be placed through a cannula or sleeve inserted through the skin that forms a working channel to the anchor location over the target bone. Anchor placement into the bony structure can be monitored endoscopically, microscopically, fluoroscopically, radiographically and/or with naked eye visualization through the cannula. Anchor placement can also be performed through micro-incisions, or through open incisions in which the skin and tissue is retracted to expose the bony structure.

In one specific technique for placing anchors 20a, 20b a guidewire of sufficient length is inserted percutaneously and anchored to the bony structure, such as a pedicle of the vertebra. The guidewire is coupled to a trackable instrument that is tracked via an image guided surgical system that generates a display on a computer monitor. With the guidewire secured at the appropriate location on the bony structure, various instruments for preparing and inserting the screw into the bony structure can be guided by the guidewire. The preparation and insertion can be monitored via a tracking instrument coupled to the various preparation and insertion instruments, and anchor extensions are mounted to the engaged anchors. The length of the connecting element between the engaged anchors is then determined with measuring instrument 100, 200 mounted to the proximal ends of the anchor extensions and manipulated as discussed above to align indicator arm 146 along or parallel to path 60 between the anchor locations and/or to position alignment members 104a, 104b or alignment members 204a, 204b in alignment with the anchor locations along the direction defined by path 60 between locations 52a, 52b.

Connecting elements 18 can be engaged on both sides of midline M of the spine, and along one or more levels of the spine. The connecting element can be engaged to stabilize adjacent vertebra in conjunction with any minimally invasive or open surgical techniques for placement of one or more implants into a disc space. For example, one or more interbody fusion devices or intervertebral spacers may be inserted into the disc space via an anterior, anterior oblique, lateral, postero-lateral, or transforaminal approach, and connecting element 18 can be positioned and engaged to the spinal column segment from a posterior approach. Further, connecting element 18 can be used to stabilize adjacent vertebrae, or any other bony structure, without placement of implants between structures comprising bony segment.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A system for measuring spacing between first and second locations in an animal subject, comprising:
    a pair of anchor extensions each including a proximal end and an opposite distal end, said distal ends being engageable in the animal subject in association with a respective one of the locations;
    a measuring instrument mountable to said proximal ends of said pair of anchor extensions, said measuring instrument including first and second articulating mechanisms engageable to and movable relative to a respective one of said pair of anchor extensions, wherein at least one of said first and second articulating mechanisms includes:
        a mounting member removably engageable to said respective one of said pair of anchor extensions;
        a first arm extending from said mounting member to a linking member opposite said mounting member;
        a second arm extending from said linking member to an alignment member opposite said linking member, wherein said first arm is rotatable about said respective anchor extension to reposition said linking member about said respective anchor extensions and said second arm is rotatable about said linking member to reposition said alignment member about said linking member; and
    said measuring instrument further including an indicator extending between and connecting said first and second articulating mechanisms to one another, said indicator including means for measuring the spacing between the first and second articulating mechanisms to provide an indication of the spacing between the first and second locations, wherein said anchor extensions each extend proximally from a respective one of the first and second locations along a mounting axis when engaged in the animal subject and said linking member of said at least one of said first and second articulating mechanisms extends along a linking axis that intersects said mounting axis of said respective anchor extension at said respective one of the first and second locations without regard to orientation of said pair of anchor extensions relative to one another.

2. The system of claim 1, wherein said indicator includes a first coupling member rotatably mounted to said first articulating mechanism and a second coupling member rotatably mounted to said second articulating mechanism, said indicator further including an indicator arm extending between said first and second coupling members.

3. The system of claim 2, wherein said indicator arm is fixed to said second coupling member and is slidably received in said first coupling member.

4. The system of claim 3, wherein said indicator arm includes a scale therealong and said first coupling member includes a window and a pointer in said window to indicate a position along said scale.

5. The system of claim 1, further comprising a pair of anchors each including a distal portion engageable to a bony segment of the animal subject, said pair of anchors further each including a proximal receiver portion defining a passageway alignable with one another to receive a connecting element, said distal ends of said pair of anchor extensions being mountable with a corresponding one of said receiver portions of said anchors.

6. The system of claim 5, wherein said pair of anchors are multi-axial screws.

7. The system of claim 1, wherein said indicator is rotatably mounted to said alignment member of each of said first and second articulating mechanisms.

8. The system of claim 1, wherein each of said alignment members extends along an alignment axis that intersects said mounting axis of said respective anchor extension at said respective one of the first and second locations.

9. The system of claim 1, wherein said indicator is articulably mounted to each of said first and second articulating mechanisms.

10. A system for measuring spacing between first and second locations in an animal subject, comprising:
   a pair of anchor extensions each including a proximal end and an opposite distal end, said distal ends being engageable in the animal subject in association with a respective one of the locations;
   a measuring instrument including first and second articulating means mountable to said proximal end of a respective one of said pair of anchor extensions, said first and second articulating means each further including a corresponding alignment member with said first and second articulating means operable to move said corresponding alignment member around said respective anchor extension and position said corresponding alignment member in alignment with a respective one of the locations, wherein at least one of said first and second articulating means includes:
      a mounting member removably engageable to said respective one of said pair of anchor extensions;
      a first arm extending from said mounting member to a linking member opposite said mounting member;
      a second arm extending from said linking member to said corresponding alignment member thereof opposite said linking member, wherein said first arm is rotatable about said respective anchor extension to reposition said linking member about said respective anchor extension and said second arm is rotatable about said linking member to reposition said alignment member about said linking member; and
   said measuring instrument further including an indicator extending between and connecting said alignment members to measure a spacing between said alignment members to provide an indication of the spacing between the first and second locations, wherein said anchor extensions each extend proximally from a respective one of the first and second locations along a mounting axis when engaged in the animal subject and said linking member of said at least one of said first and second articulating mechanisms extends along a linking axis that intersects said mounting axis of said respective anchor extension at said respective one of the first and second locations without regard to orientation of said pair of anchor extensions relative to one another.

11. The system of claim 10, wherein said indicator is rotatably mounted to said alignment members.

12. The system of claim 11, wherein said indicator includes a first coupling member rotatably mounted to a first one of said alignment members and a second coupling member rotatably mounted to the other of said alignment members, said indicator further including an indicator arm extending between said first and second coupling members.

13. The system of claim 12, wherein said indicator arm is fixed to said second coupling member and is slidably received in said first coupling member.

14. The system of claim 13, wherein said indicator arm includes a scale therealong and said first coupling member includes a window and a pointer in said window to indicate a position along said scale.

15. The system of claim 10, wherein each of said alignment members extends along an alignment axis that intersects said mounting axis of said respective anchor extension at said respective one of the first and second locations.

16. The system of claim 10, wherein:
   said first and second locations define a path that extends from the first location to the second location;
   said indicator includes an elongated indicator arm extending between and connecting said first and second articulating means; and
   said first and second articulating means are movable relative to said pair of anchor extensions and said indicator arm to position said indicator arm in parallel relation to said path without regard to orientation of said pair of anchor extensions relative to one another.

17. The system of claim 1, wherein:
   the first and second locations define a path that extends from the first location to the second location;
   said indicator includes an elongated indicator arm extending between and connecting said first and second articulating mechanisms; and
   said first and second articulating mechanisms are movable relative to said pair of anchor extensions and said indicator arm to position said indicator arm in parallel relation to said path without regard to orientation of said pair of anchor extensions relative to one another.

* * * * *